United States Patent
Do

(10) Patent No.: US 8,238,514 B2
(45) Date of Patent: Aug. 7, 2012

(54) ULTRA-SHORT PULSED X-RAY IMAGING

(75) Inventor: Synho Do, Lexington, MA (US)

(73) Assignee: Empire Technology Development, LLC, Wilmington, DE (US)

( * ) Notice: Subject to any disclaimer, the term of this patent is extended or adjusted under 35 U.S.C. 154(b) by 238 days.

(21) Appl. No.: 12/640,705

(22) Filed: Dec. 17, 2009

(65) Prior Publication Data
US 2011/0150170 A1 Jun. 23, 2011

(51) Int. Cl.
*H05G 1/26* (2006.01)
(52) U.S. Cl. .......................................... 378/16; 378/106
(58) Field of Classification Search .................... 378/16, 378/19, 106
See application file for complete search history.

(56) References Cited

U.S. PATENT DOCUMENTS

| | | | |
|---|---|---|---|
| 5,249,123 A | 9/1993 | Hsieh | |
| 5,265,013 A | 11/1993 | King et al. | |
| 5,331,682 A | 7/1994 | Hsieh | |
| 7,003,071 B2 | 2/2006 | Nagaoka et al. | |
| 7,580,170 B2 | 8/2009 | Tanaka et al. | 359/9 |
| 7,580,620 B2 | 8/2009 | Raskar et al. | 396/55 |
| 7,584,075 B2 | 9/2009 | Kim | 702/183 |
| 7,590,510 B2 | 9/2009 | Kim | 702/183 |
| 7,596,470 B2 | 9/2009 | Kim | 702/183 |
| 7,597,265 B2 | 10/2009 | Bonalle et al. | 235/487 |
| 7,597,890 B2 | 10/2009 | Chinnaiyan et al. | 424/133.1 |
| 7,605,961 B2 | 10/2009 | Klug et al. | 359/9 |
| 7,616,306 B2 | 11/2009 | Brady et al. | 356/326 |
| 7,616,735 B2 | 11/2009 | Maciunas et al. | 378/69 |
| 2005/0036582 A1 | 2/2005 | Nagaoka et al. | |
| 2005/0039849 A1 | 2/2005 | Finetti et al. | |
| 2009/0238330 A1* | 9/2009 | Luhta et al. | 378/19 |

FOREIGN PATENT DOCUMENTS

| WO | WO 03/017842 A1 | 6/2003 |
|---|---|---|
| WO | WO 2006/064403 A2 | 6/2006 |

OTHER PUBLICATIONS

Steeghs, D., Extending Emission-Line Doppler Tomography: Mapping-Modulated Line Flux, Copyright 2003 RAS, MNRAS 344,448-454.

Fenwick, JD et al., Quality Assurance of a Helical Tomotherapy Machine, Phys Med Biol. Jul. 7, 2004; 49(13):2933-53. PubMed PMID: 15285257.

Vaquero et al., "Assessment of a New High-Performance Small-Animal X-Ray Tomograph", IEEE Transactions on Nuclear Science, vol. 55, No. 3, Jun. 2008 Abstract; Sections II, IIA and IVA.

International Search Report and Written Opinion dated Nov. 16, 2010 in PCT/US2010/051414.

(Continued)

*Primary Examiner* — Hoon Song
(74) *Attorney, Agent, or Firm* — Turk IP Law, LLC

(57) ABSTRACT

Technologies are generally described for employing ultra-short pulsed X-rays in X-ray computer tomography. Timing parameters of binary modulation applied to the X-rays at the source may be adjusted based on detector characteristics, industry standards, and/or user input. The timing for minimum X-ray intensity during each pulse may be selected to minimize afterglow effect. The timing for the maximum X-ray intensity may then be determined based on one or more of the minimum X-ray intensity timing, desired X-ray dosage, and/or other similar parameters.

26 Claims, 10 Drawing Sheets

OTHER PUBLICATIONS

J.R. Duflou et al., "Towards Self-Disassembling Products Design Solutions for Economically Feasible Large-Scale Disassembly", D. Brissaud et al. (eds.), Innovation in Life Cycle Engineering and Sustainable Development, 87-110, 2006 Springer. Printed in the Netherlands.

Fenwick et al., Quality Assurance of Helical Tomotherapy Machine; Phys. Med. Biol. 49 (2004) 2933-2953.

D. Steeghs, Extending Emission-Line Doppler Tomography Mapping Modulated Line Flux; Mon. Not. R. Astron. Soc. 344, (2003) 448-454.

Carmi, R. et al., "Resolution enhancement of X-ray CT by spatial and temporal MLEM deconvolution correction," Nuclear Science Symposium Conference Record 2004 IEEE, pp. 2765-2768, Oct. 16-22, 2004.

Gupta, R. et al., "Ultra-high resolution flat-panel vol. CT: fundamental principles, design architecture, and system characterization," European radiology, vol. 16(6), pp. 1191-1205, Jun. 2006, Epub Mar. 10, 2006.

Thibault, J-B. et al., "High Quality Iterative Image Reconstruction for Multi-Slice Helical CT," International Conference on Fully 3D Reconstruction in Radiology and Nuclear Medicine, Saint Malo, 2003, pp. 4.

\* cited by examiner

COMPUTER PROGRAM PRODUCT 1000

SIGNAL-BEARING MEDIUM 1002

1004 AT LEAST ONE OF

ONE OR MORE INSTRUCTIONS FOR DETERMINING DETECTOR DISSIPATION CHARACTERISTIC(S);
    ONE OR MORE INSTRUCTIONS FOR CONFIGURING TIMING OF BINARY MODULATION OF EMITTED X-RAY PULSE;
    ONE OR MORE INSTRUCTIONS FOR COLLECTING DETECTED X-RAY DATA;
    ONE OR MORE INSTRUCTIONS FOR GENERATING IMAGE OF SUBJECT BASED ON COLLECTED DATA.

| COMPUTER-READABLE MEDIUM 1006 | RECORDABLE MEDIUM 1008 | COMMUNICATIONS MEDIUM 1010 |

FIG. 10

ULTRA-SHORT PULSED X-RAY IMAGING

BACKGROUND

Unless otherwise indicated herein, the materials described in this section are not prior art to the claims in this application and are not admitted to be prior art by inclusion in this section.

Computed tomography (CT) is a medical imaging method employing tomography created by computer processing. Digital geometry processing is used to generate a three-dimensional image of the inside of an object (e.g. human body) from a large series of two-dimensional X-ray images taken around a single axis of rotation. Although the term "computed tomography" usually refers to the computation of tomography from X-ray images, it may also be used to describe positron emission tomography and single photon emission computed tomography.

The present disclosure appreciates that there are several limitations with modern X-ray CT systems. While modern X-ray CT systems improve resolution and reduce dosage (exposure of human subjects to X-rays during tomography) by improving system geometry and materials of detector, their detector response time may present certain limitations. The afterglow effect may cause resolution degradation and artifacts in the resulting image. These afterglow effects may become more severe when the X-ray detector's size is smaller and common detector materials (i.e. gadolinium oxysulfide or selenium based materials) are used.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 10 illustrates a block diagram of an example computer program product, all arranged in accordance with at least some embodiments described herein.

DETAILED DESCRIPTION

Figure 1:
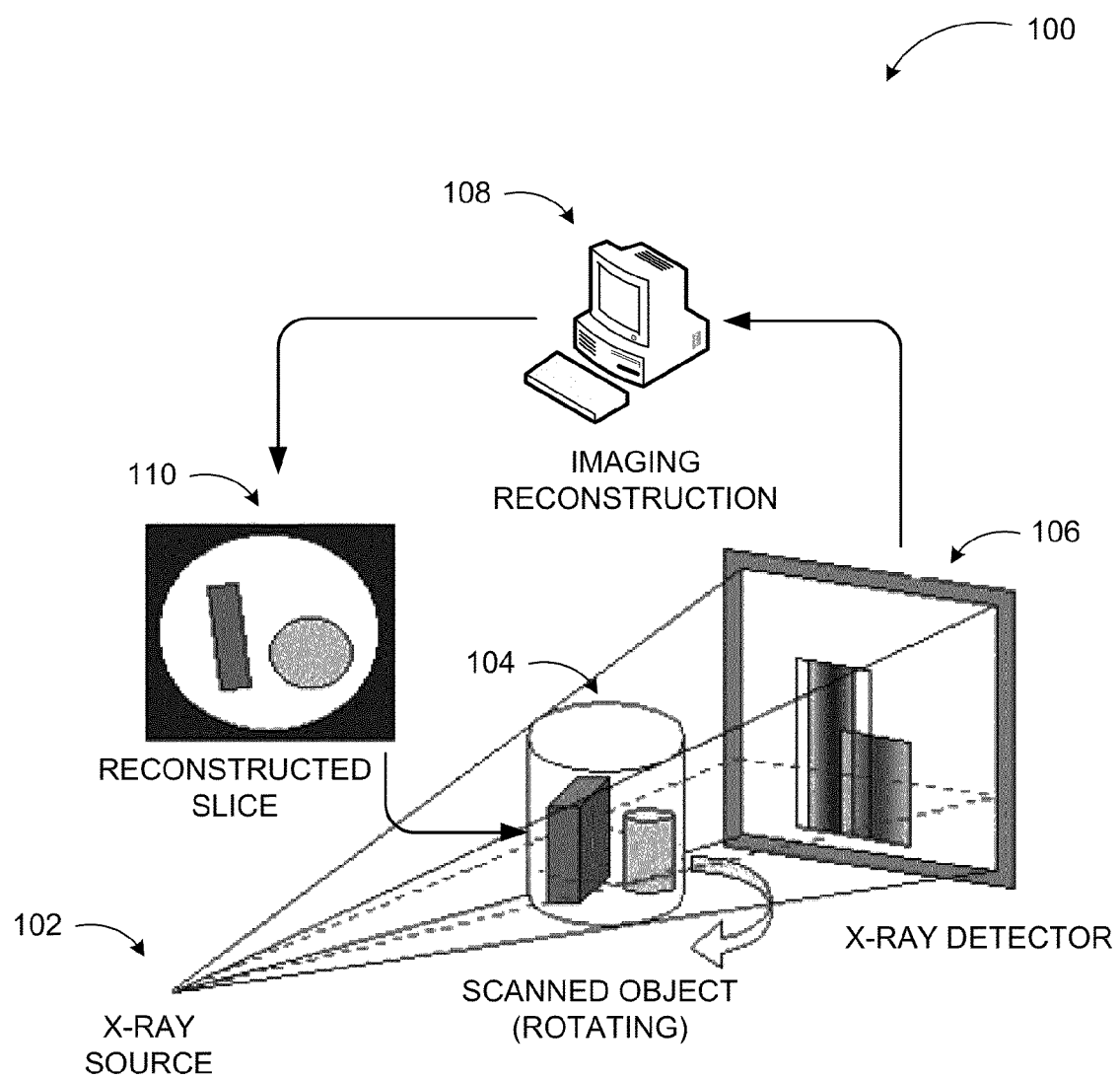
FIG. 1 illustrates an example X-ray CT system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to use of binary modulated X-ray emissions in computer tomography imaging.

Briefly stated, timing parameters of binary modulation applied to the X-rays at the source may be adjusted based on detector characteristics, industry standards, and/or user input. The timing for minimum X-ray intensity during each pulse may be selected to minimize afterglow effect. The timing for the maximum X-ray intensity may then be determined based on the minimum X-ray intensity timing, desired X-ray dosage, and similar parameters.

FIG. 1 illustrates diagram 100 of an example X-ray CT system arranged in accordance with at least some embodiments described herein. The example X-ray computer tomography system can include an X-ray source 102, an X-ray detector 106, and/or a computing system 108 adapted to reconstruct image(s). In an example operation, an object 104 can be placed between the X-ray source 102 and the X-ray detector 106. The X-ray source 102 is adapted to emit X-rays towards the object 104. The object 104 can be rotated while it is exposed to the X-rays emitted from X-ray source 102. For example, the object 104 may be placed on a platform such as a turntable, which may rotate the object 104 as it is exposed to X-rays. The X-ray detector 106 can be adapted to generate image data responsive to the X-rays emitted relative to object 104. Computing system 108 may be adapted to reconstruct an image from the image data, where the reconstructed image may correspond to a particular image (or slice) of the object relative to a particular position (e.g., angular or rotational position) of the scanned object 104. A three dimensional image may then be formed by computing system 108 using two or more of the reconstructed images.

Computing system 108 may be a general purpose computing device or a special purpose computing device that may be comprised as a standalone computer, a networked computer system, a general purpose processing unit (e.g., a microprocessor, a micro-controller, a digital signal processor or DSP, etc.), a special purpose processing unit (e.g., an specialized controller, or similar devices. Computing system 108 may be adapted to control the rotational position of the object 104, the amount of X-rays emitted by the X-ray source 102 (dosage) and/or operational parameters of the X-ray detector 106. The presently described object 104 is not limited to humans or animals, and may also include inanimate objects. For example, object 104 may comprise an automobile engine that may be scanned for quality control (e.g. component tolerances, degradation) after the engine is assembled in the automotive industry. In some applications, the dosage (e.g., exposure time, emission level, etc.) of the X-rays may need to be limited for safety or comparable concerns. However, reduced dosage may result in poorer image quality.

Figure 2:
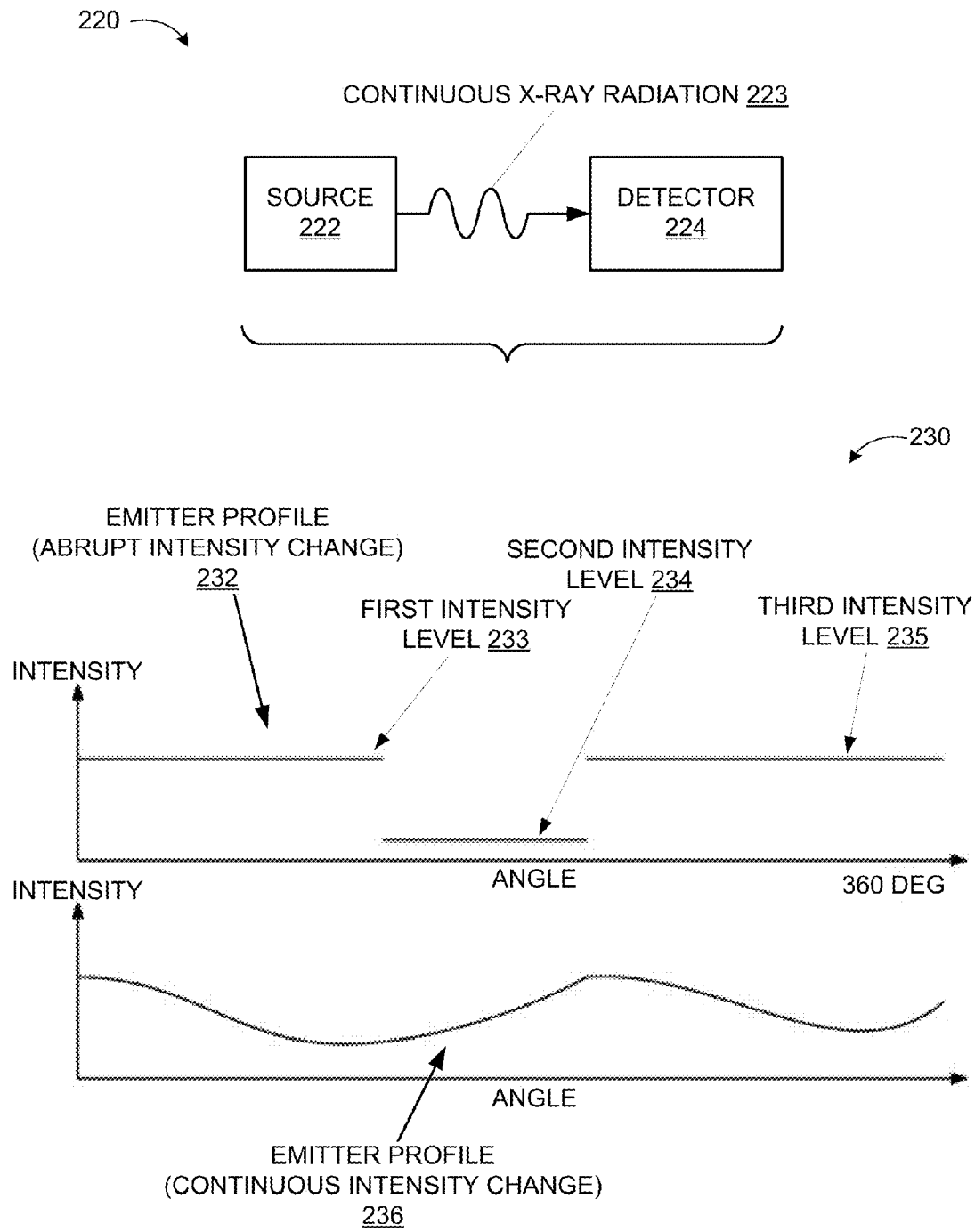
FIG. 2 illustrates an example X-ray CT system employing continuous modulation of X-rays.

FIG. 2 illustrates an example X-ray CT system employing continuous modulation of X-rays. FIG. 2 is to be contrasted with the presently disclosed subject matter shown in FIG. 3. In particular, FIG. 2 shows that a source 222, such as an X-ray emitting device, is adapted to emit continuous X-ray radiation 223. This continuous X-ray radiation 223 can be detected by a detector device 224. An example system may be implemented in a "gantry", which can be defined as the combination of the source/emitter device 222 and the detector device 224 used for X-ray imaging. The gantry may further include a revolving platform to rotate the object as it is exposed to X-rays. A computing system as previously described above can be coupled to the gantry and adapted to control operational parameters of the source 222 and/or the detector device 224, and may also be adapted to receive detection data to reconstruct slice (e.g., two dimensional or cross-sectional images) and/or three dimensional images.

As the emitted intensity graph 230 in FIG. 2 shows, emitters may have different profiles. Emitter profile 232 (top graph) is for systems that vary emitter intensity in an abrupt manner. For example, the emitter may emit at a first intensity level 233, then abruptly change to second intensity level 234, and then abruptly change to third intensity level 235. First and third intensity levels (233, 235) may also be the same. Other emitters may vary the intensity of X-rays in a more continuous manner as shown by emitter profile 236 (bottom graph) for continuous intensity change. As illustrated by emitter profile 236, the intensity level may increase and decrease continuously as the gantry rotates from 0 to 360 degrees around the subject (e.g. a patient).

Figure 3:
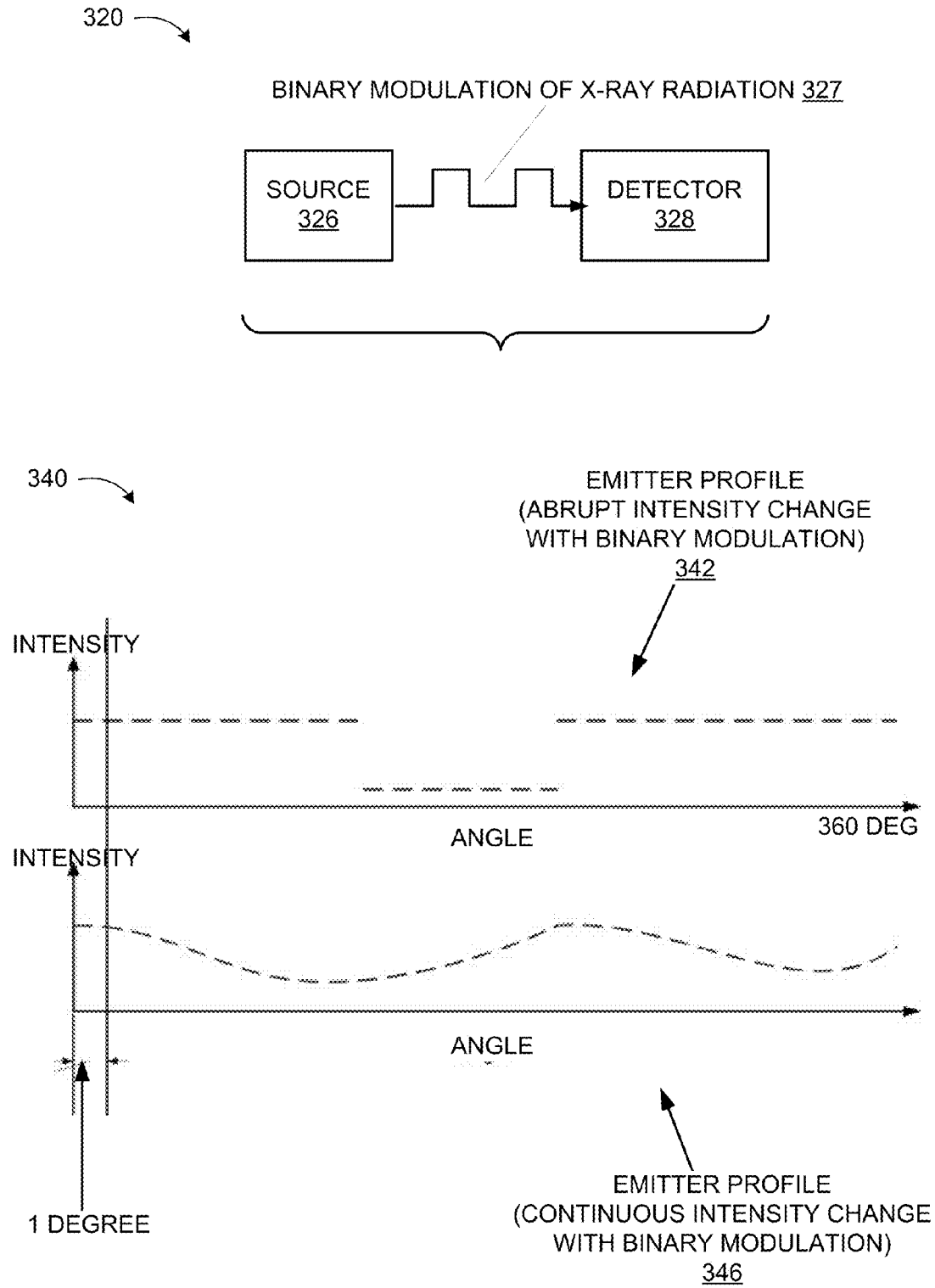
FIG. 3 illustrates use of pulsed modulation in the system of FIG. 2.

FIG. 3 illustrates use of pulsed modulation in the system of FIG. 2, arranged in accordance with at least some embodiments described herein. As shown in FIG. 3, an example system can include a source 326 that is configured to generate binary modulated X-ray pulses 327 to be received by detector 328. Thus, per emitted intensity graph 340, the emitted intensity profile 342 (top graph) for systems that vary emitter intensity level abruptly may be the same as those shown in emitter profile 232 of FIG. 2, but in FIG. 3 the X-ray is pulsed ("on" pulse, followed by an "off" interval, followed by an "on" pulse, and so on). Pulse modulation is shown in emitter profile 342 by a dashed line meant to represent the pulsed X-ray 327. As emitter profile 346 (bottom graph) for continuous intensity change systems shows, the binary modulated intensity is similar to that shown in emitter profile 236 of FIG. 2, with the difference that in emitter profile 346 (bottom) the intensity signal waveform is a pulsed waveform.

Figure 4:
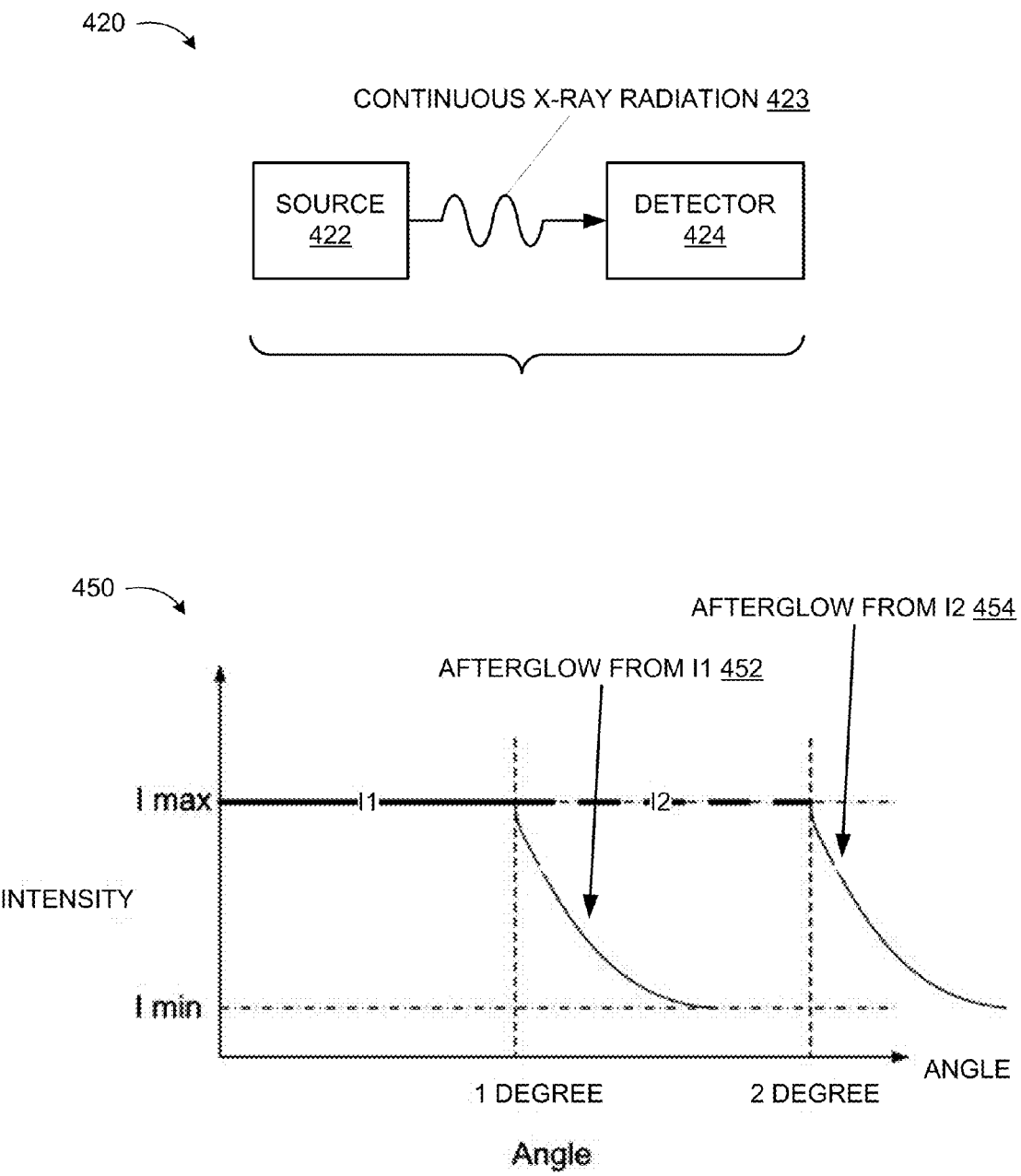
FIG. 4 illustrates the afterglow effect of continuous modulation in an X-ray CT system.
Figure 5:
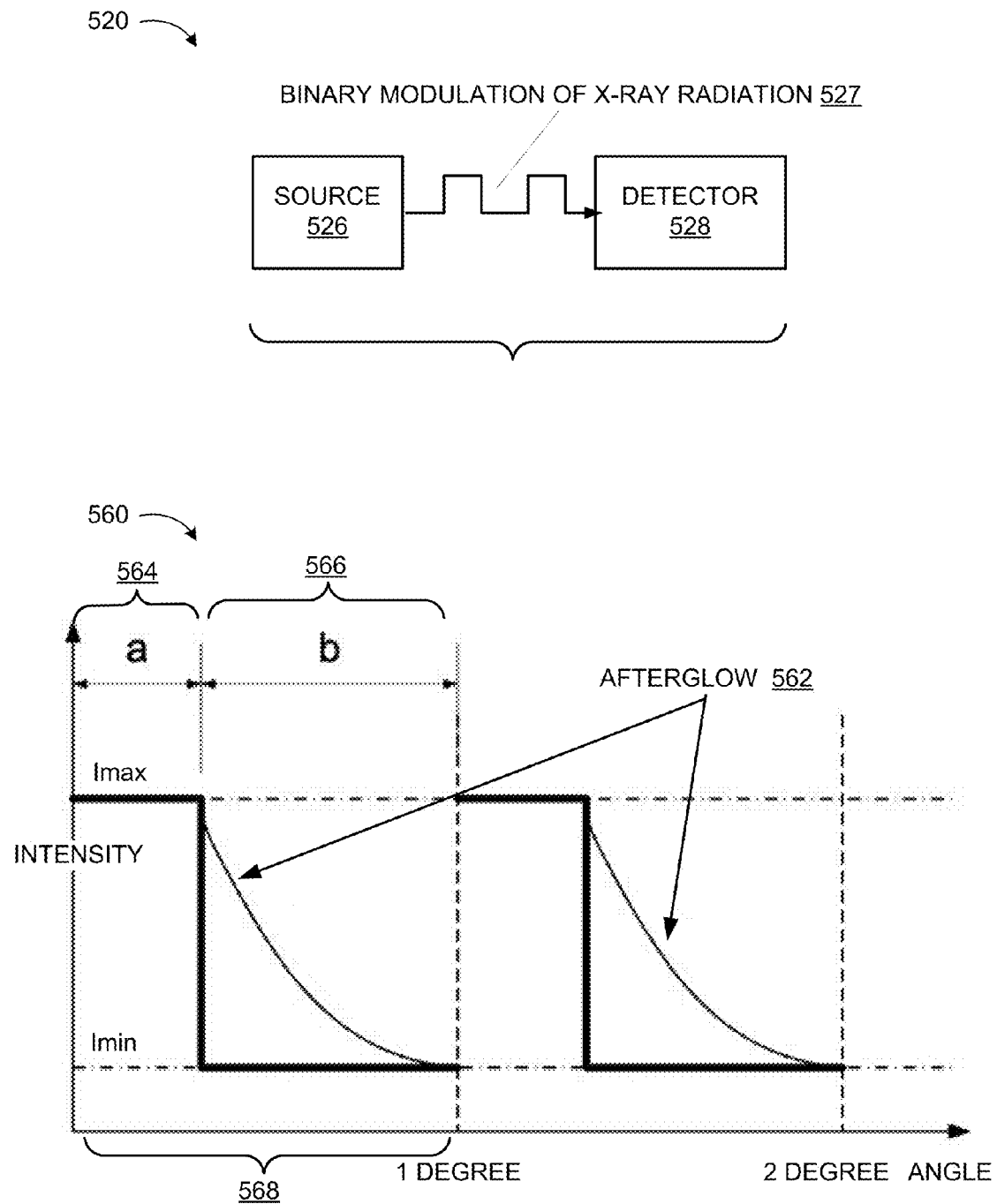
FIG. 5 illustrates the afterglow effect of pulsed modulation in an X-ray CT system.

FIG. 4 illustrates the afterglow effect of continuous modulation in an X-ray CT system, while FIG. 5 illustrates the afterglow effect of pulsed modulation in an X-ray CT system, arranged according to at least some example described herein. The difference between FIG. 2 and FIG. 3 may be correspondingly shown in FIG. 4 and FIG. 5, where the focus is on the afterglow effect at the detector devices 424 and 528. The source/X-ray/detector systems (422, 423, 424 and 526, 527, 528) in diagrams 420 and 520 of FIG. 4 and FIG. 5 are the same as those in FIG. 2 and FIG. 3.

An example X-ray detector may be constructed with a scintillator and a solid state photodiode. The scintillator is configured to emit light in the form of photons when X-rays strike the surface of the scintillator, where the photons are absorbed by the photodiode and thereby create an electric current. However, the light is not emitted by the scintillators instantaneously. Thus, the emission follows a multi-exponential decay curve. As the detector reads X-rays through the object about the object (e.g. human subject), the detector readings may blur together for successive views as a result of the exponential decay. The process may include rotating the object between stationary source and detector, rotating the detector and/or source around the stationary object, or combinations of these. This blurring, due to the response time lag of the detector, can be referred to as "afterglow" and can degrade the azimuthal component of the image resolution. The azimuthal direction of the image area can be perpendicular to a line from the center of the imaging aperture. The amount of blurring may increase the farther the object is spaced from the aperture center, since the speed at which the object is swept across the detectors effectively increases with this spacing. The effect of the afterglow blurring may round the edges of the waveform and may extend the object signal into several adjacent views. When the views are used to reconstruct an image, the object may appear enlarged and lack sharp, distinct edges.

Per FIG. 4, when the source 422 emits a continuous X-ray radiation 423, the afterglow effect may last beyond the gantry having moved past 1 degree (see graph 450 labeled Afterglow from I1, 452). Similar effect can be observed for the second current level (I2 and its afterglow 454 "spilling over" the 2 degree mark). In contrast, graph 560 in FIG. 5 shows that a pulsed X-ray that only lasts a part of the degree interval (from 0 degree to 1 degree), has an afterglow that dissipates to a low level much more quickly. Thus, afterglow spillage 562 is much more limited in FIG. 5 than it is in FIG. 4.

A formula may be devised for the amount of radiation dose or "gain" ("G"). This formula may be summarized in terms of parameter "a", which is the interval of maximum intensity (parameter "Imax") of X-ray emission, and parameter "b", which is the interval of minimum intensity of X-ray emission (parameter "Imin"), as:

$$G = \frac{a*I\max + b*I\min}{(a+b)*I\max} *100 \qquad [1]$$

As mentioned above, gain "G" can be understood as the amount of radiation dose that an object (e.g. human subject) being scanned receives, and the other parameters, "a", "b", "Imax" and "Imin" may be adjusted so that objects receive the appropriate amount of X-ray dosage. Some objects may be more sensitive to X-rays than others, yet the X-ray dosages must be substantial enough to yield accurate scanning results. The reduction of afterglow is a limitation of detectors (e.g. detector 528). The above-described factors can be taken into account when configuring a gantry, per the equation above. Using a pulsed system can reduce the afterglow effect, everything else being somewhat equal (patient considerations, X-ray image quality, etc.).

The example illustrated by graph 560 in FIG. 5 visually shows how this formula may be implemented using parameters "a", "b", "Imax" and "Imin." The degree interval 568 that corresponds to 1 degree of turn of the gantry corresponds to the sum of parameters "a" 564 and "b" 566. Thus, after a pulsed emission of X-ray energy at a maximum amplitude level (e.g., parameter "Imax") for a portion 564 of one degree as noted by parameter "a", the intensity level decays down to some minimum intensity level (e.g., parameter "Imin"), which may be either zero or non-zero. The afterglow effect occurs after the X-ray pulse at the maximum amplitude level ("Imax") has expired and is a result of the detector 528 not having the ability to instantaneously dissipate the X-ray radiation, which decays asymptotically as shown in FIG. 5 by the afterglow curve.

In another example, the minimum intensity parameter "Imin" may be set to zero, and the overall gantry system may be configured such that the afterglow effect is effectively zero when the gantry is done rotating one degree. In FIG. 5, once the rotational position of the gantry approaches the end of the degree interval 568, the afterglow has effectively dissipated to zero. According to some embodiments, the detector 528 specifications may be consulted to determine what afterglow properties it has (and, it should be noted, in different embodiments, the detector 528 specification may be determined by querying the detector to determine its afterglow response). Once the afterglow characteristics of the detector 528 are known, parameter "b" may be determined from the afterglow characteristics. For example, if the afterglow effect is substantial because of a lot of radiation being detected, the detector 528 being physically small, or the detector 528 being a low-end detector, then "b" may be large. If, on the other hand, the detector 528 is a high end detector that dissipates radiation quickly, "b" may be smaller.

Once parameter "b" is determined, parameter "a" may be determined. For example, since (a+b) is equal to 1 degree of turn of the gantry, parameter "a" can be determined from the expression "a=1−b". The gain parameter "G" may be determined as a function of parameter "Imax" offset by constant values for parameters "a" and "b". In an example scenario where parameter "b" is pushed to its limit by being made as small as possible (so that the afterglow expires just as the gantry reaches the end of its one degree of turning), "a" may be made as large as possible, since the sum of "a" and "b" is constant over a one degree turn. Thus, being able to adjust "a" and "b" may allow operators of the X-ray CT system to maintain radiation exposure of an object approximately constant at different X-ray intensity levels. In other words, looking at FIG. 5, the amount of X-ray dosage is the area defined by the product parameters "a" and "Imax" (i.e., dosage area=a*Imax). The area may be defined by different variations of the parameters resulting in the same product. For example, in one scenario "a=0.5" and "Imax=2", which yields the same X-ray radiation dosage as "a=0.25" and "Imax=4", with the difference being that in the former scenario less radiation ("Imax=2") is being used than in the latter scenario ("Imax=4").

For example, in a scenario where afterglow occurs for 20% of every degree of turn of the gantry (i.e., "b=0.2", and "a=0.8", where 1 degree=a+b) the operator (or some automated program) may adjust the amount of radiation anywhere from "a=0.8" down to a lower value ("a" may not be quite equal to zero, since that may require an infinite "Imax" spike). Parameter "Imax" may be adjustable or it may be set as an industry standard, in which case since the dosage gain "G" may be determined as a function of parameter "Imax", where the dosage gain may be calculated from one or more of parameters "a", "b", and "Imax." It should be noted that in the present discussion, parameter "Imin" has been set to a value of zero for simplicity of discussion, but it can alternatively be any non-zero value that is less than parameter "Imax."

In still another example, if the radiation dosage is a standard industry value, and parameter "a" has a value less than one degree that is also standard (e.g. the radiation dosage for half a degree of a turn), and parameter "Imin" may be set to a standard value of zero, then manufacturers may determine the value of parameter "b". This value of parameter "b" dictates which detectors should be used with a gantry.

In a further example, if the detectors are high quality such that parameter "b" has a small value (e.g. 0.1-0.2), and parameter "a" has a value that is at the low end of industry standard values (e.g. approximately 0.25), then parameters "a" and "b" may be compressed by having the gantry speed up the rotational cycle. In FIG. 5, the afterglow dissipates as a function of time, thus, if there is room per degree given small values for parameters "a" and "b", then the gantry may rotate at speeds up to the afterglow limits of the detectors.

Figure 6:
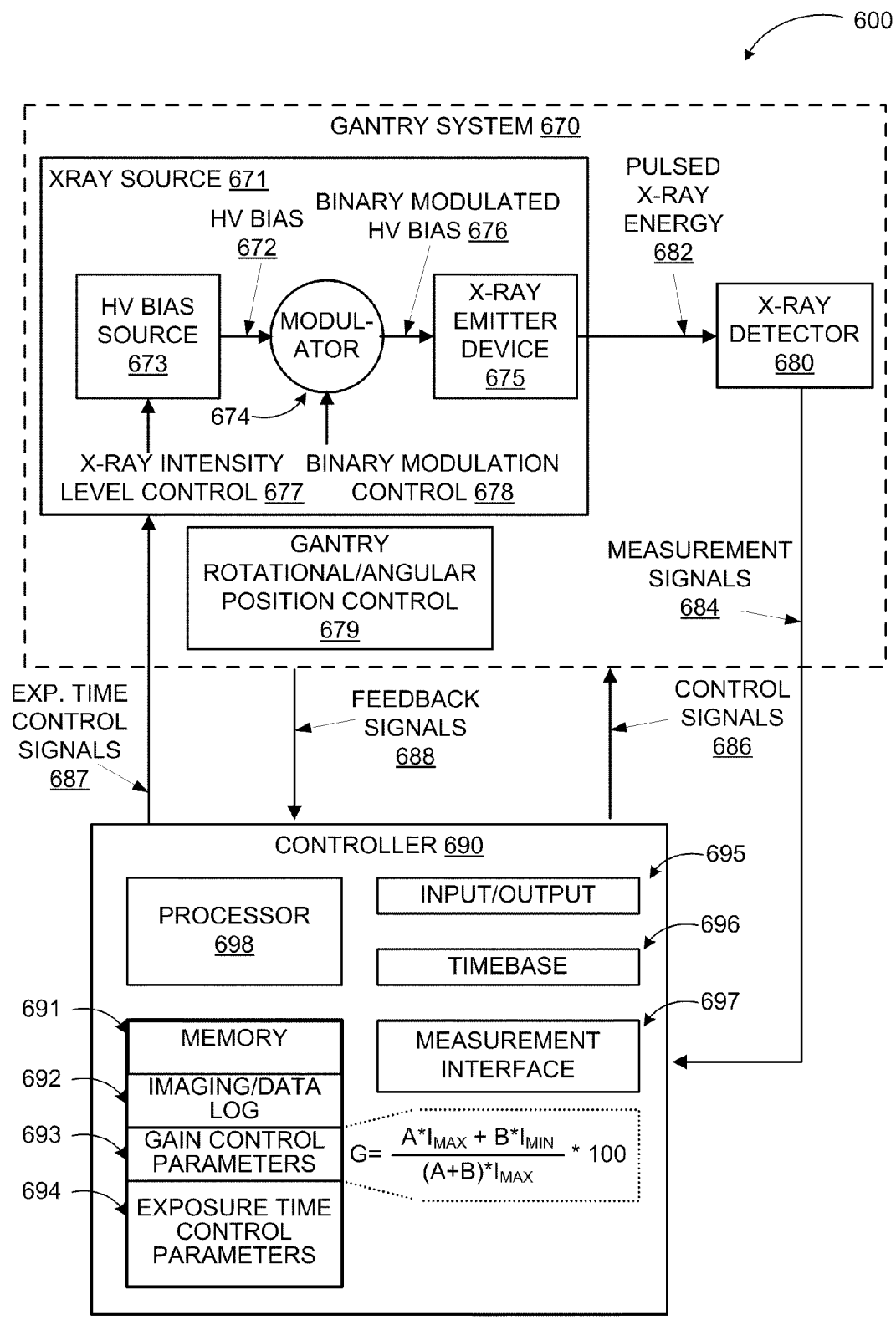
FIG. 6 illustrates a gantry system and a controller mechanism, where ultra-short pulsed X-ray imaging.

FIG. 6 illustrates diagram 600 of a gantry system and a controller mechanism, where ultra-short pulsed X-ray imaging according to at least embodiments described herein may be implemented. In this figure, gantry system 670 is the controlled source of X-rays (pulsed X-ray energy 682). X-ray source 671 of the gantry system 670 may include a high voltage (HV) bias source 673, whose output, HV bias 672, is modulated by modulator 674. Modulator 674 converts HV bias 672 into binary modulated HV bias 676 based on the modulation input, binary modulation control 678. Binary modulated HV bias 676 is used to control the X-ray emitter device 675, which emits pulsed X-ray energy 682. At least a portion of the emitted energy can be detected by X-ray detector 680. X-ray detector 680 may either be an integral part of the gantry system 670 (which may be rotatable around the subject) or a separate device.

Several aspects of the gantry system's operation can be controlled by controller 690. Some of these aspects may include the binary modulation, exposure time, X-ray intensity level, and the rotational/angular position of the gantry to scan an object. Controller 690 may also collect data and/or measurement signals from X-ray detector 680 in a time logged manner (timebase 696) such that the image-data for the X-ray image(s) can be captured.

Returning to the controllable/configurable aspects of the gantry system 670, a rotational speed and/or angular position of the gantry may be controlled through control signals 686 and/or feedback signals 688 exchanged between controller 690 and gantry rotational/angular position control module 679. Binary modulation control signal 678 may be provided to modulator 674 directly by the controller 690 or indirectly (e.g. through another module of the gantry system 670). Exposure time and X-ray intensity may be adjusted through signals provided by the controller 690 to the HV bias source 673. One such signal may be X-ray intensity level control 677. Another example is exposure time control signals 687, which enables control of the exposure time at the HV bias source 673 through controller 690.

In some example embodiments, modulator 674 may control the pulse modulation electronically. In another example (not shown), however, the modulator may be replaced by a mechanical shutter that opens and closes in order to produce a pulsing X-ray effect from the X-ray emitter device 675.

As can be seen in diagram 600, equation [1] discussed above can govern the gain or dosage "G". The controller may include a processor 698, a memory 691, input and output mechanisms 695, a timebase 696, and/or a measurement interface 697 (e.g. a data collection module). Memory 691 may include memory storage locations that may be adapted to store imaging data and/or control parameters such as an imaging data log 692, gain control parameters 693, exposure time control parameters 694, and other parameters. Controller 698 may be configured to control how the gantry system behaves via the control signals 686 and/or feedback signals 688. The control signals 686 from the controller 690 and/or the feedback signals 688 from the gantry system 670 may be used to adjust appropriate parameters such as those discussed above (e.g., binary modulation control 678, etc.). Controller 690 may also be adapted to receive and/or measurement signals 684 from the X-ray detector 680 through a measurement interface 697. X-ray imaging data may also be captured by the controller 690 via the measurement interface 697.

A system arranged according to various embodiments described herein may employ binary modulation at the single angle level as shown in FIG. 3 and FIG. 4. For one complete rotation (360°), CT scanners may generate continuous X-ray flux through whole rotation as shown in FIG. 3. This may cause the contamination of measurement by the afterglow of previous angle. In some cases, the intensity level may be changed by the shape of objects or even the cardiac cycle in cardiac imaging. By implementing ultra short X-ray emissions for each angular position for the X-ray source rather than continuous illumination, recovering function on detector can be treated as an impulse response function that has exponential shape in the time domain. In X-ray detection technology, physically smaller detectors (e.g. 10-50 $mm^2$) provide slower response time (e.g. 80-100 μs). Thus, example systems may employ smaller detector elements that are limited by their slow response, X-ray dosage in human applications may be reduced without compromising image quality, and afterglow effects may be reduced while increasing overall image quality.

While embodiments have been discussed above using specific examples, components, and configurations, they are intended to provide a general guideline to be used for improving X-ray CT scanning systems through pulsed X-rays. These examples do not constitute a limitation on the embodiments, which may be implements using other components, adjustment schemes, and configurations using the principles described herein. For example, control mechanisms for X-ray sources may be implemented using general purpose computing devices, special purpose computing devices, special controllers, and the like. Control of parameters such as gain, exposure time, etc. may be implements through specific algorithms executed by such computing devices.

Figure 7:
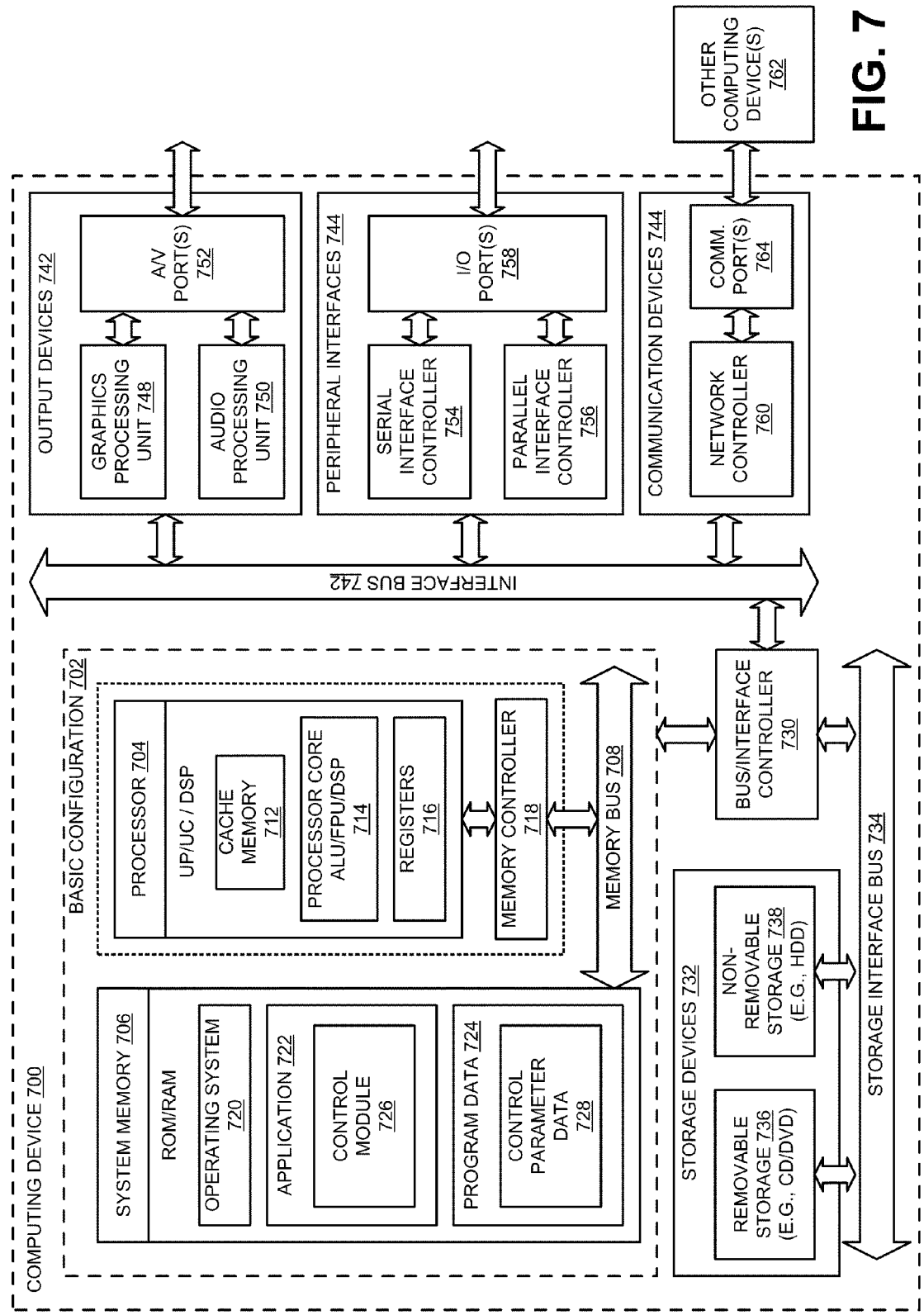
FIG. 7 illustrates a general purpose computing device, which may be used to implement pulsed X-ray imaging.

FIG. 7 illustrates an example general purpose computing device 700, which may be used to implement ultra-short pulsed X-ray imaging according to present disclosure. In a very basic configuration 702, computing device 700 typically includes one or more processors 704 and a system memory 706. A memory bus 708 may be used for communicating between processor 704 and system memory 706.

Depending on the desired configuration, processor 704 may be of any type including but not limited to a microprocessor (μP), a microcontroller (μC), a digital signal processor (DSP), or any combination thereof. Processor 704 may include one more levels of caching, such as a level cache memory 712, a processor core 714, and registers 716. Example processor core 714 may include an arithmetic logic unit (ALU), a floating point unit (FPU), a digital signal processing core (DSP Core), or any combination thereof. An example memory controller 718 may also be used with processor 704, or in some implementations memory controller 718 may be an internal part of processor 704.

Depending on the desired configuration, system memory 706 may be of any type including but not limited to volatile memory (such as RAM), non-volatile memory (such as ROM, flash memory, etc.) or any combination thereof System memory 706 may include an operating system 720, one or more applications 722, and program data 724. Application 722 may include a control module 726 that is arranged to adjust operational parameters of a gantry system such as one or more of gain, exposure time, or modulation as discussed above. Program data 724 may include one or more of imaging data, time log, control parameter data 728 (e.g. gain control parameters, exposure time control parameters), and similar data as discussed above in conjunction with FIG. 6. This data may be useful for controlling a gantry system in using ultra-short pulsed X-rays as is described herein. In some embodiments, application 722 may be arranged to operate with program data 724 on operating system 720 such that ultra-short pulsed X-rays are used in a CT system as described herein. This described basic configuration 702 is illustrated in FIG. 7 by those components within the inner dashed line.

Computing device 700 may have additional features or functionality, and additional interfaces to facilitate communications between basic configuration 702 and any required devices and interfaces. For example, a bus/interface controller 730 may be used to facilitate communications between basic configuration 702 and one or more data storage devices 732 via a storage interface bus 734. Data storage devices 732 may be removable storage devices 736, non-removable storage devices 738, or a combination thereof Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 706, removable storage devices 736 and non-removable storage devices 738 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of computing device 700.

Computing device 700 may also include an interface bus 740 for facilitating communication from various interface devices (e.g., output devices 742, peripheral interfaces 744, and communication devices 746) to basic configuration 702 via bus/interface controller 730. Example output devices 742 include a graphics processing unit 748 and an audio processing unit 750, which may be configured to communicate to various external devices such as a display or speakers via one or more AN ports 752. Example peripheral interfaces 744 include a serial interface controller 754 or a parallel interface controller 756, which may be configured to communicate with external devices such as input devices (e.g., keyboard, mouse, pen, voice input device, touch input device, etc.) or other peripheral devices (e.g., printer, scanner, etc.) via one or more I/O ports 758. An example communication device 746 includes a network controller 760, which may be arranged to facilitate communications with one or more other computing devices 762 over a network communication link via one or more communication ports 764.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 700 may also be implemented as a personal computer including both laptop computer and non-laptop computer configurations. Moreover computing device 700 may be implemented as a networked system or as part of a general purpose or specialized server.

Figure 8:
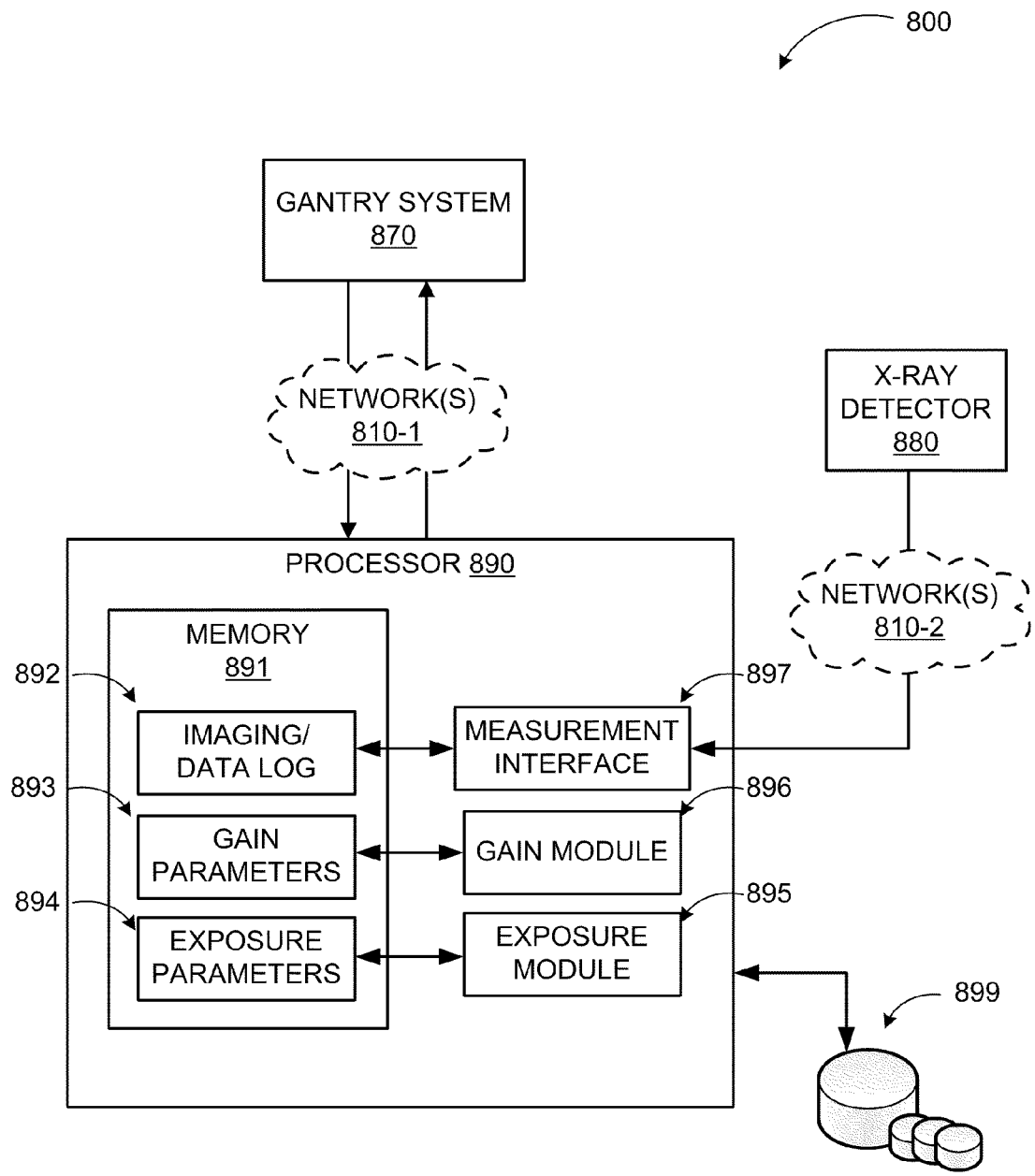
FIG. 8 illustrates a special purpose processor, which may be used to implement pulsed X-ray imaging.

FIG. 8 illustrates a special purpose processor, which may be used to implement pulsed X-ray imaging according to at least embodiments described herein. Gantry system 870 in diagram 800 can be, for example, as described in FIG. 6. Processor 890 may include special modules such as measurement interface module 897, gain control module 896, and exposure control module 895. These modules may employ data including, but not limited to, imaging data 892, gain parameters 893, exposure parameters 894, which may be stored in memory 891 or according to other embodiments in remote data stores 899. Processor 890 may be configured to receive X-ray detection data from X-ray detector 880 through operable coupling (wired or wireless) or through networks 810-2. By executing instructions for its special modules, processor 890 may control operational parameters of the gantry system 870 operable coupling (wired or wireless) or through networks 810-1.

Network(s) 810-1 and 810-2 may comprise any topology of servers, clients, switches, routers, modems, Internet service providers, and any appropriate communication media (e.g., wired or wireless communications). A system according to embodiments may have a static or dynamic network topology. Network(s) 810-1 and 810-2 may include a secure network such as an enterprise network (e.g., a LAN, WAN, or WLAN), an unsecure network such as a wireless open network (e.g., IEEE 802.11 wireless networks), or a world-wide network such (e.g., the Internet). Network(s) 810-1 and 810-2 may also comprise a plurality of distinct networks that are adapted to operate together. Network(s) 810-1 and 810-2 are configured to provide communication between the nodes described herein. By way of example, and not limitation, network(s) 810-1 and 810-2 may include wireless media such as acoustic, RF, infrared and other wireless media. Furthermore, network(s) 810-1 and 810-2 may be portions of the same network or separate networks.

Example embodiments may also include methods. These methods can be implemented in any number of ways, including the structures described herein. One such way is by machine operations, of devices of the type described in the present disclosure. Another optional way is for one or more of the individual operations of the methods to be performed in conjunction with one or more human operators performing some of the operations while other operations are performed by machines. These human operators need not be collocated with each other, but each can be only with a machine that performs a portion of the program. In other examples, the human interaction can be automated such as by pre-selected criteria that is machine automated.

Figure 9:
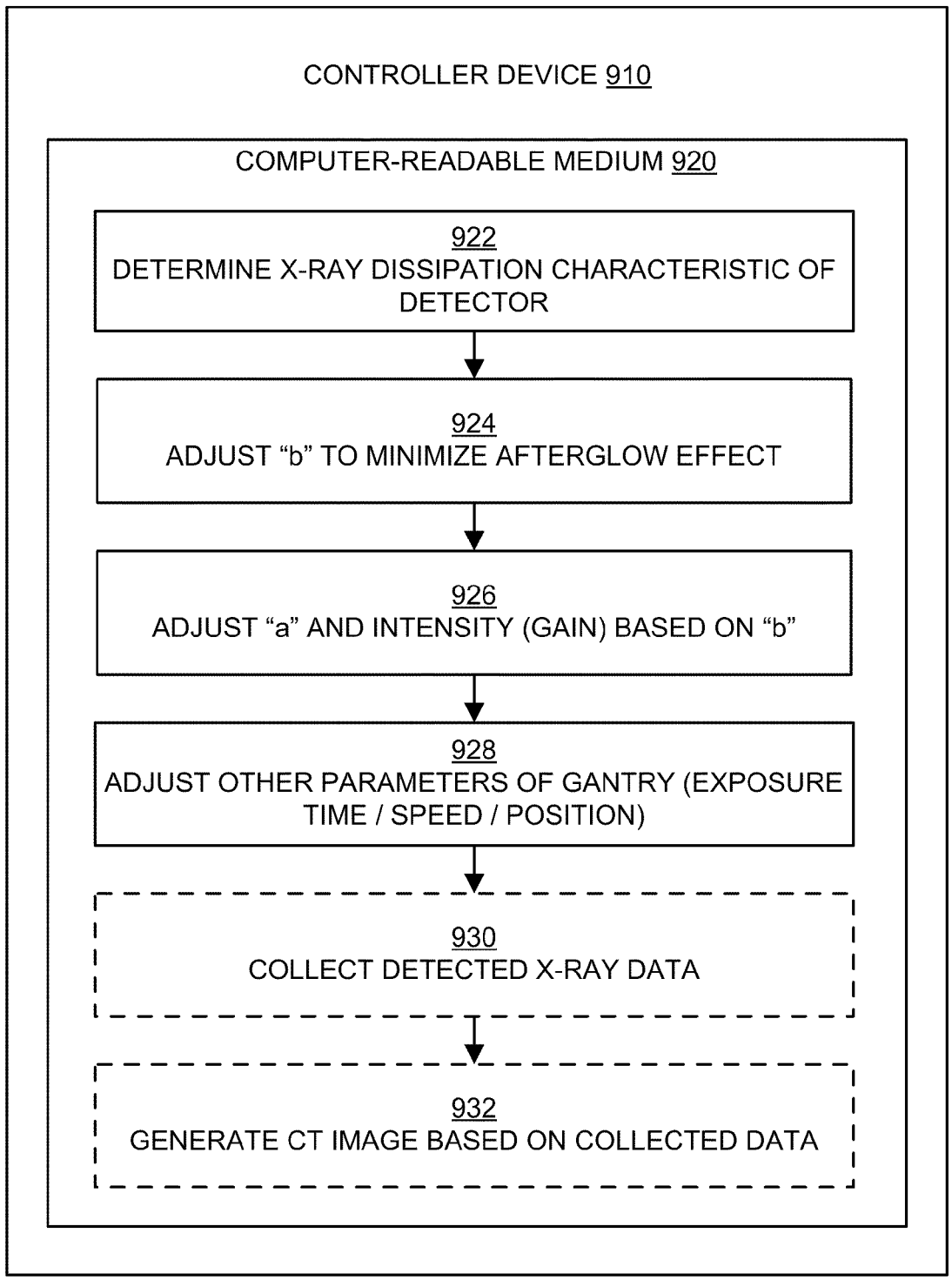
FIG. 9 is a flow diagram illustrating an example method that may be performed by a computing device such as device 700 in FIG. 7 or processor 890 in FIG. 8.

FIG. 9 is a flow diagram illustrating an example method that may be performed by a computing device such as device 700 in FIG. 7 or processor 890 in FIG. 8, arranged in accordance with at least some embodiments described herein. The operations described in blocks 922 through 932 may be stored as computer-executable instructions in a computer-readable medium such as computer-readable medium 920 of controller device 910.

A process of employing binary modulated X-rays in computer tomography may begin with operation 922, "DETERMINE X-RAY DISSIPATION CHARACTERISTIC OF DETECTOR". At operation 922, the X-ray dissipation characteristic(s) of a detector (e.g. size of the detection module, quality of the detector, etc.) may be determined by a processor of a computing device e.g. processor 704 of computing device 700) looking up the detector's characteristics in a database or by querying the detector for its characteristic(s).

Operation 922 may be followed by operation 924, "ADJUST "a" TO MINIMIZE AFTERGLOW EFFECT." At operation 924, a timing parameter of the binary modulation, a portion of a degree interval where X-ray intensity is minimum (designated as "b" in FIG. 5), may be adjusted to attenuate the afterglow effect.

Operation 924 may be followed by operation 926, "ADJUST "a" AND INTENSITY (GAIN) BASED ON "b"." At operation 926, another timing parameter, a portion of the degree interval where X-ray intensity is maximum (designated as "a" in FIG. 5), may be adjusted by a controller such as controller 690 of FIG. 6 based on the value of "b" set at operation 924. This adjustment may also define a gain of the system or an X-ray dosage (e.g. average, peak, minimum, etc.).

Operation 926 may be followed by operation 928, "ADJUST OTHER PARAMETERS OF GANTRY (EXPOSURE/TIME/SPEED/POSITION)." At operation 928, other parameters of the gantry such as exposure time, rotational speed, and/or angular position may be adjusted by the controller (e.g. controller 690 of FIG. 6). This is followed by optional operation 930, where X-ray data from the X-ray detector is collected by the processor or controller (e.g. controller 690 of FIG. 6 through its measurement interface 697). The collected data may be used by the same or another processor to generate a CT image of the subject at optional operation 932. As discussed previously, the processors and controllers performing these operations are example illustrations and should not be construed as limitations on embodiments. The operations may also be performed by other computing devices or modules integrated into a single computing device or implemented as separate machines.

The operations included in process 900 are for illustration purposes. Ultra-short pulsed X-ray imaging may be implemented by similar processes with fewer or additional operations. In some examples, the operations may be performed in a different order. In some other examples, various operations may be eliminated. In still other examples, various operations may be divided into additional operations, or combined together into fewer operations.

FIG. 10 illustrates a block diagram of an example computer program product 1000 arranged in accordance with at least some embodiments described herein. In some examples, as shown in FIG. 10, computer program product 1000 may include a signal bearing medium 1002 that may also include machine readable instructions 1004 that, when executed by, for example, a processor, may provide the functionality described above with respect to FIG. 7, FIG. 8, and FIG. 9. Thus, for example, referring to processor 890, one or more of the modules 896 and/or 895 may undertake one or more of the tasks shown in FIG. 10 in response to instructions 1004 conveyed to the gantry system 870 by medium 1002 to perform actions associated with controlling the gantry system employing ultra-short pulsed X-rays as described herein. Some of those instructions may include determining an X-ray dissipation characteristic of a detector device; configuring a timing of a binary modulation applied to the X-rays based on the dissipation characteristic of the detector device to minimize an afterglow effect of the detected X-rays by: adjusting a first portion of a degree interval during which a binary modulated X-ray pulse is emitted from a source device and adjusting a second portion of the degree interval during which the X-ray pulse is emitted at maximum intensity radiation based on a value of the first portion of the degree interval;

collecting detected X-ray data as a gantry comprising a source device and the detector device rotates around the subject at steps equal to the degree interval; and generating an image of the subject based on the collected data.

In some implementations, signal bearing medium 1002 depicted in FIG. 10 may encompass a computer-readable medium 1006, such as, but not limited to, a hard disk drive, a Compact Disc (CD), a Digital Video Disk (DVD), a digital tape, memory, etc. In some implementations, signal bearing medium 1002 may encompass a recordable medium 1008, such as, but not limited to, memory, read/write (R/W) CDs, R/W DVDs, etc. In some implementations, signal bearing medium 1002 may encompass a communications medium 1010, such as, but not limited to, a digital and/or an analog communication medium (e.g., a fiber optic cable, a waveguide, a wired communications link, a wireless communication link, etc.). Thus, for example, program product 1000 may be conveyed to one or more modules of the processor 890 by an RF signal bearing medium 1002, where the signal bearing medium 1002 is conveyed by a wireless communications medium 1010 (e.g., a wireless communications medium conforming with the IEEE 802.11 standard).

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g. as one or more programs running on one or more microprocessors), as firmware, or as virtually any combination thereof, and that designing the circuitry and/or writing the code for the software and or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity of gantry systems; control motors for moving and/or adjusting components and/or quantities).

A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for performing X-ray computer tomography imaging of a subject using pulse modulated X-rays, the method comprising:
   determining an X-ray dissipation characteristic of a detector device; and
   configuring a timing of a binary modulation applied to the X-rays based on the dissipation characteristic of the detector device such that an afterglow effect of the detected X-rays is substantially minimized by:
      adjusting a portion of a degree interval during which a binary modulated X-ray pulse is emitted from a source device at minimum intensity radiation; and
      adjusting another portion of the degree interval during which the X-ray pulse is emitted at maximum intensity radiation based on a value of the portion of the degree interval.

2. The method according to claim 1, wherein the portion of the degree interval is increased in response to at least one from a set of: the detector device detecting X-rays above a predefined threshold, a detection aperture of the detector device being smaller than another predefined threshold, and the detector device being a low quality detector device.

3. The method according to claim 1, wherein the portion of the degree interval is decreased in response to the detector device being configured to dissipate detected X-ray radiation rapidly.

4. The method according to claim 1, wherein the portion of the degree interval is determined based on one or more of: receiving dissipation characteristic information from a database and/or receiving dissipation characteristic information by querying the detector device.

5. The method according to claim 1, further comprising:
   determining a portion of the degree interval during which the X-ray pulse is emitted at minimum intensity radiation based on one or more of: a user selection and/or an industry standard;

determining a range for another portion of a degree interval during which a binary modulated X-ray pulse is emitted from a source device based on a value of the portion of the degree interval; and selecting a detector for the detector device based on the range for the other portion of the degree interval.

6. The method according to claim 5, wherein the portion and the other portion of the degree interval are selected such that a speed of an X-ray gantry comprising a source device and the detector device is adjustable while the afterglow effect of the detected X-rays is substantially minimized.

7. The method according to claim 1, wherein the degree interval comprises one-three-hundred-and-sixtieth of a circumference of a circle and a source device and the detector device form part of an X-ray imaging gantry that is adapted to rotate 360 degrees about the subject.

8. An apparatus for attenuating afterglow in medical imaging of a subject, the apparatus comprising:
a detector device;
a source device configured to emit a binary modulated pulse once per a degree interval, wherein a maximum intensity radiation of the pulse is limited to a portion of the degree interval and
a controller device configured to:
determine a dissipation characteristic of the detector device; and
configure a timing of the binary modulated pulse based on the dissipation characteristic of the detector device to substantially minimize an afterglow effect in detected X-rays by one or more of:
adjusting a second portion of a degree interval during which the binary modulated pulse is emitted at minimum intensity radiation from the source device; and
adjusting a first portion of the degree interval during which the binary modulate pulse is emitted at maximum intensity radiation.

9. The apparatus according to claim 8, wherein the maximum intensity radiation is substantially constant over the first portion of the degree interval.

10. The apparatus according to claim 8, wherein a minimum intensity radiation is substantially constant over the second portion of the degree interval.

11. The apparatus according to claim 8, wherein the degree interval comprises one-three-hundred-and-sixtieth of a circumference of a circle.

12. The apparatus according to claim 8, wherein the emitted binary modulated pulse is X-ray radiation.

13. The apparatus according to claim 8, wherein the source device and the detector device form part of an X-ray imaging gantry that is adapted to rotate 360 degrees about the subject.

14. An apparatus for controlling an X-ray emitting source device to attenuate afterglow in imaging of a subject through binary modulation, comprising:
a memory configured to store operational parameters associated with a gantry comprising the source device and a detector device;
a processor coupled to the memory, wherein the processor is configured to:
determine a dissipation characteristic of the detector device; and
configure a timing of the binary modulation applied to the X-rays based on the dissipation characteristic of the detector device to substantially minimize an afterglow effect in the detected X-rays by one or more of:

adjusting a second portion of a degree interval during which a binary modulated X-ray pulse is emitted at minimum intensity radiation from a source device; and adjusting a first portion of the degree interval during which the X-ray pulse is emitted at maximum intensity radiation.

15. The apparatus according to claim 14, wherein the processor is further configured to control one or more of: a gain of the source device, an exposure time, a rotation speed of the gantry, and/or an angular position of the gantry.

16. The apparatus according to claim 15, wherein the gain is controlled based on the expression:

$$G = \frac{a*I\max + b*I\min}{(a+b)*I\max} * 100,$$

where "a" is the first portion of the degree interval, "b" is the second portion of the degree interval, "Imax" is a maximum intensity of X-ray emission, and "Imin" is a minimum intensity of X-ray emission.

17. The apparatus according to claim 16, wherein Imin is set to zero.

18. The apparatus according to claim 16, the processor is further configured to:
select a minimum value for "b" such that the afterglow effect is substantially minimized; and
adjust "a" to arrive at a desired X-ray intensity level.

19. A non-transitory computer-readable storage medium having instructions stored thereon for attenuating afterglow in medical imaging of a subject, the instructions comprising:
determining an X-ray dissipation characteristic of a detector device;
configuring a timing of a binary modulation applied to the X-rays based on the dissipation characteristic of the detector device to minimize an afterglow effect of the detected X-rays by:
adjusting a second portion of a degree interval during which a binary modulated X-ray pulse is emitted at minimum intensity radiation from a source device; and
adjusting a first portion of the degree interval during which the X-ray pulse is emitted at maximum intensity radiation based on a value of the second portion of the degree interval;
collecting detected X-ray data at a gantry comprising a source device and the detector device rotates around the subject at steps substantially equal to the degree interval; and
generating an image of the subject based on the collected data.

20. The non-transitory computer-readable storage medium of claim 19, wherein a sum of the first portion of the degree interval and the second portion of the degree interval is substantially equal to the degree interval.

21. The non-transitory computer-readable storage medium of claim 19, wherein the instructions further comprise:
adjusting the first portion of the degree interval such that a product of the first portion of the degree interval and the maximum X-ray intensity is maintained constant and the maximum X-ray intensity is selected based on a user input.

22. A system for performing X-ray computer tomography imaging of a subject using pulse modulated X-rays, comprising:
- a source device configured to emit a binary modulated pulse once per a degree interval, wherein a maximum intensity radiation of the pulse is limited to a first portion of the degree interval;
- a detector device configured to receive the emitted the binary modulated pulse; and
- a controller operable to configure a timing of the binary modulation applied to the X-rays based on the dissipation characteristic of the detector device to substantially minimize an afterglow effect in the detected X-rays by one or more of:
    - adjusting a second portion of a degree interval during which a binary modulated X-ray pulse is emitted at a substantially minimum intensity radiation from a source device; and
    - adjusting the first portion of the degree interval during which the X-ray pulse is emitted at a substantially maximum intensity radiation.

23. The system according to claim 22, wherein the source device and the detector device are integral parts of a gantry configured to rotate about the subject.

24. The system according to claim 22, wherein the controller is further configured to control one or more of: an exposure time, a gain, a rotational speed, and/or an angular position associated with the gantry using control signals based on input from one or more of: feedback signals from the gantry, measurement signals from the detector device, and/or a user input.

25. The system according to claim 22, wherein the controller includes one or more of: a general purpose computing device, a special purpose computing device, and/or a special purpose controller.

26. The system according to claim 22, wherein the detector device includes one or more of: a scintillator and a solid state photo diode.

* * * * *